United States Patent
Sato et al.

(10) Patent No.: US 8,592,781 B2
(45) Date of Patent: Nov. 26, 2013

(54) METHOD AND APPARATUS FOR QUANTITATIVE EVALUATION OF WALL ZETA-POTENTIAL, AND METHOD AND APPARATUS FOR QUANTITATIVE VISUALIZATION OF SURFACE MODIFICATION PATTERN

(75) Inventors: Yohei Sato, Yokohama (JP); Yutaka Kazoe, Yokohama (JP); Shu Miyakawa, Yokohama (JP)

(73) Assignee: Keio University, Tokyo (JP)

( * ) Notice: Subject to any disclaimer, the term of this patent is extended or adjusted under 35 U.S.C. 154(b) by 332 days.

(21) Appl. No.: 13/120,041

(22) PCT Filed: Sep. 25, 2009

(86) PCT No.: PCT/JP2009/066652
§ 371 (c)(1),
(2), (4) Date: Mar. 21, 2011

(87) PCT Pub. No.: WO2010/041560
PCT Pub. Date: Apr. 15, 2010

(65) Prior Publication Data
US 2011/0174988 A1 Jul. 21, 2011

(30) Foreign Application Priority Data
Oct. 10, 2008 (JP) .................. 2008-263639

(51) Int. Cl.
*G01N 21/64* (2006.01)
(52) U.S. Cl.
USPC ....................................... 250/459.1
(58) Field of Classification Search
USPC ...................................... 250/459.1
See application file for complete search history.

(56) References Cited

U.S. PATENT DOCUMENTS 5,093,266 A * 3/1992 Leader et al. .................. 436/68
2002/0109840 A1 8/2002 Wolleschensky et al.

FOREIGN PATENT DOCUMENTS

| JP | A-2002-125696 | 5/2002 |
| JP | A-2002-168870 | 6/2002 |

(Continued)

OTHER PUBLICATIONS

Yutaka Kazoe and Yohei Sato, "Measurement of Zeta-Potential at Microchannel Wall by a Nanoscale Laser Induced Fluorescence Imaging." Journal of Fluid Science and Technology, vol. 2, No. 2 (2007) pp. 429-440. Released Dec. 7, 2007. <doi:10.1299/jfst.2.429> Downloaded Mar. 21, 2013.*

(Continued)

*Primary Examiner* — Constantine Hannaher
(74) *Attorney, Agent, or Firm* — Oliff & Berridge, PLC

(57) ABSTRACT

A first and a second fluorescent dye are mixed into a solution, the first dye being positively ionized in the solution and the second dye being negatively ionized in the solution and having different fluorescence wavelengths from the first dye. The solution is flown onto a measured surface, and the surface is excited with an evanescent wave to produce a fluorescence intensity distribution of two colors. A fluorescence intensity of the surface is measured using a two-dimensional imaging element, the element providing a fluorescence intensity of each color separated from the other colors, thereby calculating a ratio of the fluorescence intensities of the colors. Using an equation expressing a relationship between the ratio of fluorescence intensities and a wall zeta potential, the ratio is converted to a two-dimensional distribution of wall zeta potentials. This achieves visualizing in real time and quantitatively evaluating the two-dimensional distribution of wall zeta potentials, and surface modifications.

8 Claims, 5 Drawing Sheets

(56) References Cited

FOREIGN PATENT DOCUMENTS

JP  A-2004-502173  1/2004
JP  A-2007-085915  4/2007

OTHER PUBLICATIONS

Mark E. McGovern, Krishna M. R. Kallury, and Michael Thompson, "Role of Solvent on the Silanization of Glass with Octadecyltrichlorosilane." Langmuir, 1994, 10 (10), pp. 3607-3614. Publication date: Oct. 1994. <doi:10.1021/la00022a038> Downloaded Mar. 26, 2013.*

Sato et al., "Measurements of Temporally and Spatially Distribution of Multi-variables in Micro- and Nanoscale Investigations of Flow Structure and Ion Motion in the Vicinity of Wall," *Journal of the Japan Society of Mechanical Engineers*, 2008, pp. 88-91, vol. 111, No. 1071, Japan.

Coppeta et al., "Dual emission laser induced fluorescence for direct planar scalar behavior measurements," *Experiments in Fluids*, 1998, pp. 1-15, vol. 25.

Ichiyanagi et al., "Effects of Surface Modification Patterning on Electroosmotic Flow Characteristics in a Microchannel," *Dai 44 Kai National Heat Transfer Symposium of Japan Koen Ronbunshu*, 2007, D231.

Ichiyanagi et al., "Flow Characteristics in Microchannel with Non-uniform Zeta-Potential," *Dai 45 Kai National Heat Transfer Symposium of Japan Koen Ronbunshu*, 2008.

Whitesides et al., "Soft Lithography in Biology and Biochemistry," *Annual Review of Biomedical Engineering*, 2001, pp. 335-373, vol. 3.

Kirby et al., "Zeta potential of microfluidic substrates: I. Theory, experimental techniques, and effects on separations," *Electrophoresis*, 2004, pp. 187-202, vol. 25.

Lopez et al. "Scanning Electron Microscopy Can Form Images of Patterns in Self-Assembled Monolayers," *Langmuir*, 1993, pp. 1513-1516, vol. 9.

Yang et al., "Surface enhanced Raman imaging of a patterned self-assembled monolayer formed by microcontact printing on a silver film," *Appl. Phys. Lett.*, 1996, pp. 4020-4022, vol. 69, No. 26.

Lopez et al., "Imaging of Features on Surfaces by Condensation Figures," *Science*, 1993, pp. 647-649, vol. 260.

Oldham et al., "Streaming Potential in Small Capillaries," *Journal of Colloid Science*, 1963, pp. 328-336, vol. 18.

Sze et al., "Zeta-potential measurement using the Smoluchowski equation and the slope of the current-time relationship in electroosmotic flow," *Journal of Colloid and Interface Science*, 2003, pp. 402-410, vol. 261.

Sinton et al., "Direct and Indirect Electroosmotic Flow Velocity Measurements in Microchannels," *Journal of Colloid and Interface Science*, 2002, pp. 184-189, vol. 254.

Kazoe et al., "Effect of Ion Motion on Zeta-Potential Distribution at Microchannel Wall Obtained from Nanoscale Laser-Induced Fluorescence," *Analytic Chemistry*, 2007, pp. 6727-6733, vol. 79, No. 17.

Axelrod et al., "Total Internal Reflection Fluorescence," *Annual Review of Biophysics and Bioengineering*, 1984, pp. 247-268, vol. 13.

Sato et al., "Visualization of convective mixing in microchannel by fluorescence imaging," *Measurement Science and Technology*, 2003, pp. 114-121, vol. 14.

International Search Report issued in International Application No. PCT/P2009/066652 dated Dec. 22, 2009.

* cited by examiner

Fig. 1
(A) Wall zeta potential (absolute value) High
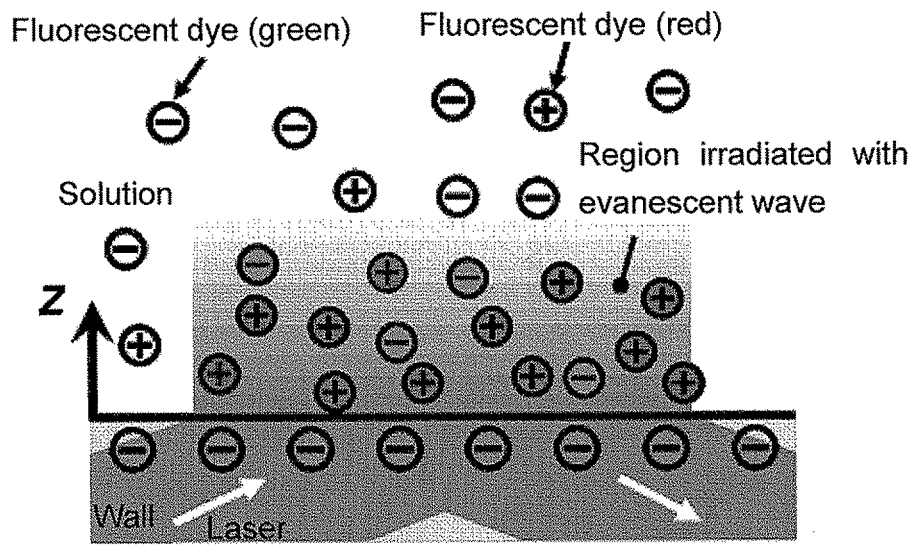
(B) Wall zeta potential (absolute value) Low
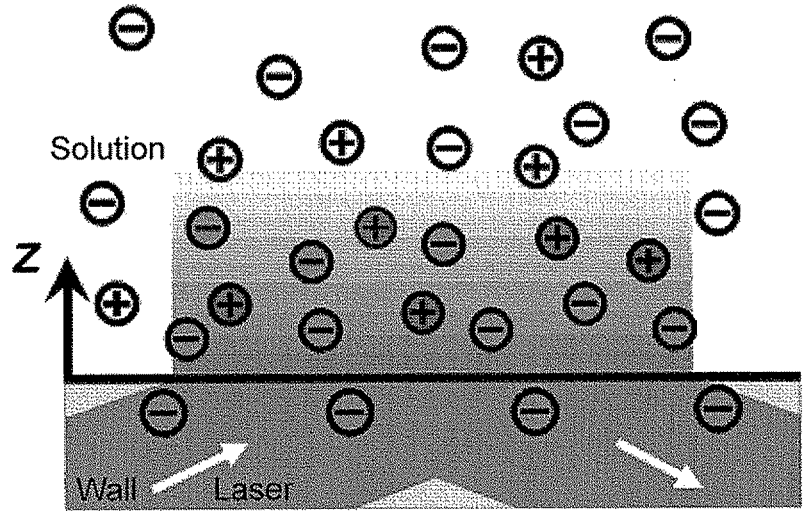

(A) Fluorescence image captured by 3CCD camera

Calibration curve applied (B) Zeta potential distribution

METHOD AND APPARATUS FOR QUANTITATIVE EVALUATION OF WALL ZETA-POTENTIAL, AND METHOD AND APPARATUS FOR QUANTITATIVE VISUALIZATION OF SURFACE MODIFICATION PATTERN

TECHNICAL FIELD

The present invention relates to a method and an apparatus for quantitatively evaluating wall zeta potential, pH, or temperature distributions, and to a method and an apparatus for quantitatively visualizing surface modifications. More particularly, the invention relates to a method and an apparatus for quantitative evaluation of wall zeta potential, pH, or temperature distributions, which is suitable for use in the fields of cell biology, electrochemistry, and micro/nano-scale thermofluid engineering. The invention further relates to a method and an apparatus for quantitative visualization of surface modifications using the quantitative evaluation method and apparatus.

BACKGROUND ART

In the field of surface science, intensive studies have been conducted on material surface properties such as adsorptivity and wettability. Surface modification techniques for forming organic monomolecular film, referred to as SAMs (Self-assembled monolayers) (see Whitesides, G. M. et al., Annu. Rev. Biomed. Eng., 3, 335-373, 2001 (hereinafter referred to as [Non-Patent Document 1])), on the surface of materials have been developed and a number of attempts have also been made to actively vary the properties of the material surface.

Recent years have seen the development of microfluidic devices that have integrated functions for separation, mixture, reaction, and detection of samples. One of crucial parameters for determining the performance of those devices that make use of electrokinetics is the zeta potential or the potential on the solid-liquid interface (see Kirby, B. J. et al., Electrophoresis, 25, 187-202, 2004 [hereinafter referred to as Non-Patent Document 2]). In the fields of electrochemistry and biochemistry, intensive studies have been made to apply patterned surface modifications to microfluidic devices to thereby control the wettability and material adsorptivity thereof.

Such studies on the material surface have led to measurement techniques for evaluating surface properties. The techniques which have been suggested include a technique for visualization of the structure of material surfaces using the electron microscope (see Lopez, G. P. et al., Langmuir, 9, 1513-1516, 1993 [hereinafter referred to as Non-Patent Document 3]), a technique for evaluation of surface modifications using the thickness of SAMs or the type of molecules contained therein (see Yang, x. M. et al., Appl. Phys. Lett., 69 (26):4020-4022, 1996 [hereinafter referred to as Non-Patent Document 4]), a technique for evaluation of surface properties using wettability (see Lopez, G. P. et al., Science, 260, 647-649, 1993 [hereinafter referred to as Non-Patent Document 5]), and the like.

For the performance evaluation and the optimum design of the microfluidic device mentioned above, it is effective to quantitatively measure the zeta potential on the flow path surface within the device. That is to say, the surface modification pattern applied onto the wall surface of flow paths in the device or the two-dimensional distribution of the zeta potential established by mixed liquid samples can be quantitatively visualized to thereby evaluate contributions to device performance.

Several methods have been devised for measuring the zeta potential in microfluidic fields. The methods include the streaming potential method (see Oldham, I. B. et al., J. Colloid Sci., 18, 328-336, 1963 [hereinafter referred to as Non-Patent Document 6]), the current monitoring method (see Sze, A. et al., J. Colloid Interface Sci., 261, 402-410, 2003 [hereinafter referred to as Non-Patent Document 7]), the method for measuring electroosmotic velocities to calculate the zeta potential using the Helmholtz-Smoluchowski equation (see Sinton, D. et al., J. Colloid Interface Sci., 254, 184-189, 2002 [hereinafter referred to as Non-Patent Document 8]), and the like. But these methods are all dedicated to the measurement of the average zeta potential across the flow path.

On the other hand, the nano-scale laser induced fluorescence imaging method developed by two of the inventors (see Kazoe, Y. and Sato, Y., Anal. Chem., 79, 6727-6733, 2007 [hereinafter referred to as Non-Patent Document 9]) was the first one which enables the measurement of a two-dimensional distribution of zeta potentials within the device. The nano-scale laser induced fluorescence imaging method employs the fluorescent dye (red) that is negatively ionized in an aqueous solution and the evanescent wave that occurs by total reflection of light on the interface between different refractive indices (see Axelrod, D. et al., Ann. Rev. Biophys. Bioeng., 13, 247-268, 1984 [hereinafter referred to as Non-Patent Document 10], and Japanese Patent Application Laid-Open No. 2007-85915 [hereinafter referred to as Patent Document 1]). The evanescent wave diminishes exponentially in intensity with increasing distance from the interface. It is thus possible to produce the wave on the wall surface of flow paths, thereby allowing an area within the distance of a few hundred nanometers from the wall to be irradiated therewith. With the fluorescent dye mixed in an aqueous solution flowing into the path, the concentration distribution of the negatively charged fluorescent dye in the vicinity of the wall surface varies depending on the wall zeta potential. Therefore, the fluorescence intensity upon excitation by the evanescent wave depends on the zeta potential. Accordingly, the distribution of the fluorescence intensity teaches the zeta potential distribution.

Note that other than the zeta potential, there are also disclosed a technique for obtaining the distribution of pH, in J. Coppeta et al., Experiments in Fluids 1-15, 1998 [hereinafter referred to as Non-Patent Document 11], and a technique for obtaining the distribution of temperatures, in Y. Sato et al., Meas. Sci. Technol. 14, 114-121, 2003 [hereinafter referred to as Non-Patent Document 12].

To obtain the two-dimensional distribution of zeta potentials according to the nano-scale laser induced fluorescence imaging method, the CCD camera is used to acquire fluorescence intensity images. However, since the acquired image may contain a fluorescence intensity distribution caused by an excitation light intensity distribution, a reference image has to be acquired to make compensation therefor. For this reason, it is difficult to visualize the two-dimensional distribution of zeta potentials from the image itself captured by the CCD camera, which is not suitable for real-time measurement. Furthermore, it is also necessary to make compensation again for different measurement positions or flow path shapes. Thus, this method has drawbacks such as measurement errors caused by shifts in position or the intricacy of the measurement technique.

DISCLOSURE OF THE INVENTION

The present invention was developed to address the aforementioned conventional problems. It is therefore an object of the present invention to make it possible to visualize in real time as well as quantitatively evaluate the two-dimensional distribution of wall zeta potentials, pHs, or temperatures and surface modifications in the microfluidic device.

For quantitative evaluation of a wall zeta potential, pH, or temperature distribution, the present invention provides a method which includes the following steps to address the aforementioned problems. That is, the method includes:

a step of mixing a first and a second fluorescent dyes into a solution, the first dye being positively ionized in the solution, and the second dye being negatively ionized in the solution and having a different fluorescence wavelength from the first dye;

a step of flowing the solution onto a measured surface;

a step of exciting the measured surface with an evanescent wave to thereby produce a fluorescence intensity distribution of the two colors according to a concentration distribution of each fluorescent dye;

a step of measuring a fluorescence intensity of the measured surface using a two-dimensional imaging element, the element being capable of providing a fluorescence intensity of each color separated from the fluorescence intensities of the two colors;

a step of calculating a ratio of the fluorescence intensities of the two colors; and a step of using a previously created equation expressing a relationship between the ratio of fluorescence intensities and a wall zeta potential, pH, or temperature to convert the distribution of the ratio of fluorescence intensities into a two-dimensional distribution of wall zeta potentials, pHs, or temperatures.

Furthermore, the present invention provides an apparatus for quantitative evaluation of a distribution of wall zeta potentials, pHs, or temperatures. The apparatus includes:

means for mixing a first and a second fluorescent dyes into a solution, the first dye being positively ionized in the solution, and the second dye being negatively ionized in the solution and having a different fluorescence wavelength from the first dye;

means for flowing the solution onto a measured surface;

means for exciting the measured surface with an evanescent wave to thereby produce a fluorescence intensity distribution of the two colors according to a concentration distribution of each fluorescent dye;

a two-dimensional imaging element being capable of providing a fluorescence intensity of each color separated from fluorescence intensities of two colors;

means for calculating a ratio of the fluorescence intensities of the two colors measured using the two-dimensional imaging element; and means for using a previously created equation expressing a relationship between the ratio of fluorescence intensities and a wall zeta potential, pH, or temperature to convert the distribution of the ratio of fluorescence intensities into a two-dimensional distribution of wall zeta potentials, pHs, or temperatures.

Here, it is possible to calibrate the relationship between the fluorescence intensity ratio and the wall zeta potential, pH, or temperature.

Furthermore, the first dye employed may be dichlorotris(1, 10-phenanthroline) ruthenium(II) hydrate, which emits red light, and the second dye may be Alexa Fluor (registered trademark) 488, which emits green light.

Furthermore, to obtain the distribution of wall pH or temperatures, the plurality of fluorescent dyes employed may be LDS698 (registered trademark) and fluoroscein.

Furthermore, the two-dimensional imaging element may be a single 3CCD camera.

The present invention also provides a method for quantitative visualization of a surface modification. The method includes:

a step of mixing a first and a second fluorescent dyes into a solution, the first dye being positively ionized in the solution, and the second dye being negatively ionized in the solution and having a different fluorescence wavelength from the first dye;

a step of flowing the solution onto a measured surface, the measured surface having a localized distribution of zeta potentials, pHs, or temperatures due to a surface modification;

a step of exciting the measured surface with an evanescent wave to thereby produce a fluorescence intensity distribution of the two colors according to a concentration distribution of each fluorescent dye;

a step of measuring a fluorescence intensity of the measured surface using a two-dimensional imaging element, the element being capable of providing a fluorescence intensity of each color separated from fluorescence intensities of the two colors;

a step of calculating a ratio of the fluorescence intensities of the two colors; and a step of using a previously created equation expressing a relationship between the ratio of fluorescence intensities and a wall zeta potential, pH, or temperature to convert the distribution of the ratio of fluorescence intensities into a two-dimensional distribution of wall zeta potentials, pHs, or temperatures, thereby visualizing a surface modification pattern.

The present invention also provides an apparatus for quantitative visualization of a surface modification. The apparatus includes:

means for mixing a first and a second fluorescent dyes into a solution, the first dye being positively ionized in the solution, and the second dye being negatively ionized in the solution and having a different fluorescence wavelength from the first dye;

means for flowing the solution onto a measured surface, the measured surface having a localized distribution of zeta potentials, pHs, or temperatures due to a surface modification;

means for exciting the measured surface with an evanescent wave to thereby produce a fluorescence intensity distribution of the two colors according to a concentration distribution of each fluorescent dye;

a two-dimensional imaging element being capable of providing a fluorescence intensity of each color separated from fluorescence intensities of the other of the two colors;

means for calculating a ratio of the fluorescence intensities of the two colors measured using the two-dimensional imaging element; and means for using a previously created equation expressing a relationship between the ratio of fluorescence intensities and a wall zeta potential, pH, or temperature to convert the distribution of the ratio of fluorescence intensities into a two-dimensional distribution of wall zeta potentials, pHs, or temperatures, thereby visualizing a surface modification pattern.

Here, the surface modification may be made by octadecyltrichlorosilane.

According to the present invention, the nano-scale laser induced fluorescence imaging method developed by one of the inventors can adopt a first fluorescent dye being positively ionized in the solution, and a second dye being negatively ionized in the solution and having a different fluorescence from the first dye, and a two-dimensional imaging element being capable of providing each color separated from the other of the two colors of the fluorescence. This makes it possible to easily visualize the two-dimensional distribution of zeta potentials, pHs, or temperatures resulting from a surface modification in a microfluidic device and conduct quantitative measurements in real time.

Furthermore, when compared with a conventional technique, the invention can reduce a significant number of steps of the measurement procedure and measurement errors in the measurement process.

Furthermore, the present invention can be used to quantitatively visualize a surface modification pattern or the two-dimensional distribution of complicated ion behaviors which are caused by the mixture or reaction of liquid samples in a microfluidic device. It will be thus possible to obtain various findings concerning a complicated fluidic field in a microfluidic thermal system. For example, the electroosmotic fluidic field that is formed depending on the zeta potential can be analyzed by knowing the zeta potential distribution. Furthermore, the invention is also useful for performance evaluation or optimum design of devices aiming to control the adsorptivity of cells or proteins or to control the wettability of wall surfaces. In addition, the invention is expected to be applicable to a wide variety of fields such as cell biology, electrochemistry, and micro fluid engineering.

BRIEF DESCRIPTION OF THE DRAWINGS

FIG. 1 is a view illustrating the principle of the present invention;

BEST MODE(S) FOR CARRYING OUT THE INVENTION

Now, the embodiment of the present invention will be explained below in more detail with reference to the accompanying drawings.

The fluorescent dyes employed in the present embodiment to determine the wall zeta potential distribution are a red fluorescent dye to be positively ionized in an aqueous solution or dichlorotris(1,10-phenanthroline) ruthenium(II) hydrate (with an excitation wavelength of 449 nm and fluorescence at 582 nm), and a negatively ionized green fluorescent dye or Alexa Fluor (registered trademark) 488 (with an excitation wavelength of 495 nm and fluorescence at 519 nm).

The two types of fluorescent dyes were dissolved in a solution (with the respective concentrations in the solution are 50 μmol/l for dichlorotris (1,10-phenanthroline) ruthe-nium(II) hydrate and 5 μmol/l for Alexa Fluor (registered trademark) 488). With the solution flown into a flow path, the concentration distributions of their respective fluorescent dyes in the vicinity of the wall surface vary depending on the wall zeta potential. As illustrated in FIG. 1(A), with the absolute value of negative wall zeta potentials being comparatively large, the red light emitting fluorescent dye or a cation has a higher concentration in the vicinity of the wall surface than the green light emitting fluorescent dye. Conversely, as illustrated in FIG. 1(B), with the absolute value of wall zeta potentials being comparatively small, the green light emitting fluorescent dye has a relatively greater concentration in the vicinity of the wall surface.

Accordingly, the vicinity of the flow path wall surface with a localized distribution of zeta potentials due to a surface modification can be excited with an evanescent wave, thereby providing a fluorescence intensity distribution according to the concentration distribution of the fluorescent dyes of the two colors. This fluorescence is captured, for example, using a 3CCD camera, whereby the two-dimensional distribution of wall zeta potential can be visualized as the distribution of a fluorescence intensity ratio between the two colors, red and green. It is thus possible to visualize the surface modification pattern.

The wall zeta potential is uniquely determined by the fluorescence intensity ratio between the dyes of two colors, and thus does not depend on the excitation light intensity distribution. This eliminates the necessity of correcting the potential with a reference image. It is thus possible to visualize the surface modification pattern in real time with a 3CCD camera image. It is also possible to remove measurement errors caused by a positional shift that may occur upon acquisition of the reference image, and further simplify the measurement technique.

Figure 2:
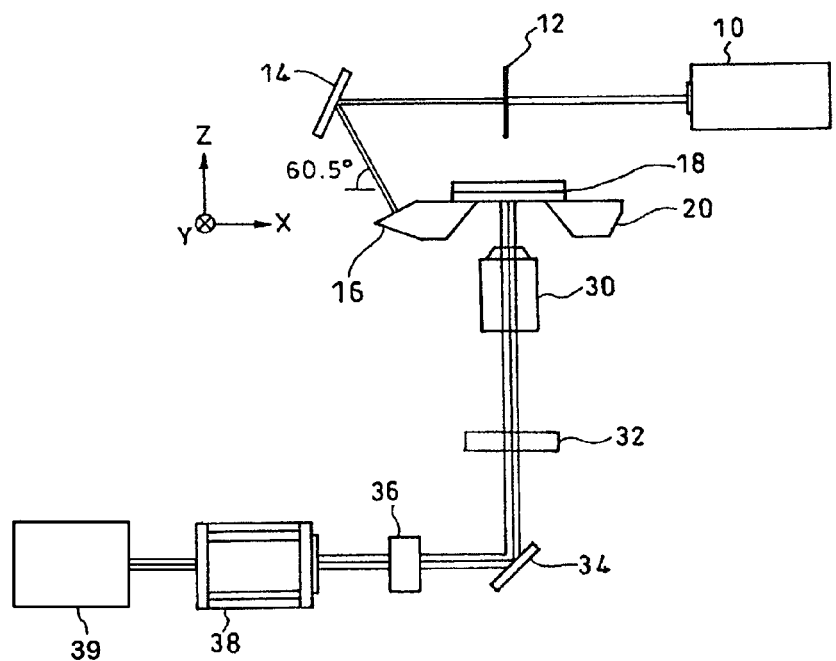
FIG. 2 is a view illustrating an entire configuration of an example of a measurement system for implementing the present invention.
Figure 3:
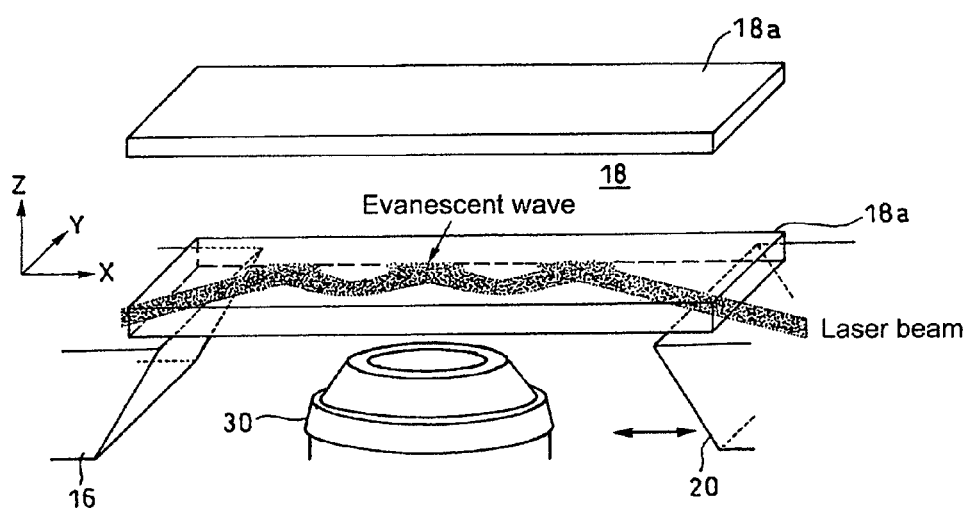
FIG. 3 is a magnified perspective view illustrating the measurement flow path portion of FIG. 2.

To implement the aforementioned evanescent wave optical measurement, the measurement system was set up as shown in FIG. 2. This system is adapted such that a means for exciting a measured surface with an evanescent wave, such as laser 10, lases a beam of light, for example, at a wavelength λ=488 nm, and the laser beam then passes through a pin hole 12 for providing a more uniform intensity distribution using light in the vicinity of the optical axis center and is reflected on a mirror 14. The laser beam is then, as shown in FIG. 3 in more detail, directed into means for flowing the solution onto a measured surface, such as glass 18a of the wall of a measurement flow path 18 via a prism 16, allowing an evanescent wave to be produced in the flow path by total reflection on the interfaces. The fluorescence from the fluorescent dyes excited by the evanescent wave is magnified, for example, with a 20× objective lens 30 having an aperture of 0.45. The fluorescent light then travels via a filter 32 for eliminating background optical noise other than the fluorescence, a mirror 34, and for example, a 1.4× magnifier lens 36 to be finally captured by a 3CCD camera 38. A means 39 for calculating a ratio of the fluorescence and for using a previously created equation expressing a relationship between the ratio of fluorescence intensities and a wall zeta potential, pH, or temperature is then used to convert the distribution of the ratio of fluorescence intensities into a two-dimensional distribution of wall zeta potentials, pHs, or temperatures.

The figure shows a movable prism 20 for creating a laser transmission optical path to accommodate different thicknesses of the glass 18a in order to prevent scattered beams of light caused by the laser beam being diffused on the glass surface (see Patent Document 1).

Figure 4:
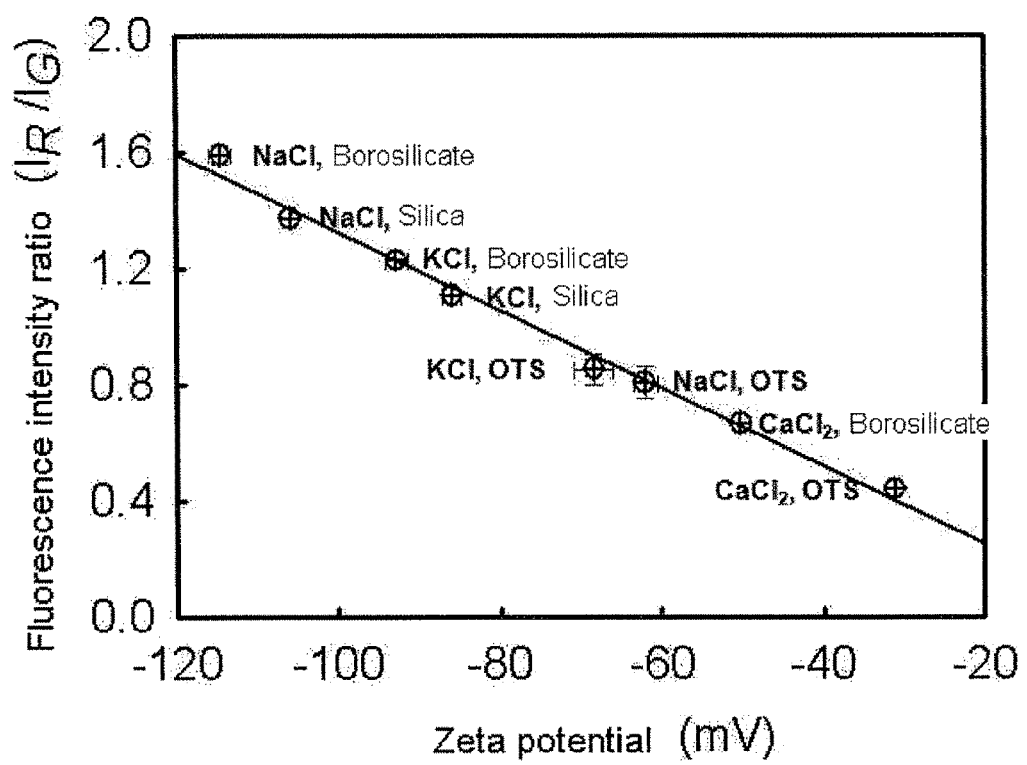
FIG. 4 is a graph showing an exemplary relationship between the fluorescence intensity ratio and the zeta potential according to an embodiment of the present invention.

Furthermore, the fluorescence intensity ratio between the fluorescent dyes of two colors to be measured and the wall zeta potential can be calibrated, thereby quantitatively evaluating the wall zeta potential distribution resulting from a surface modification. As shown in Table 1 (the solution used for the calibration) and Table 2 (the material of the flow path wall used for the calibration), the fluorescence intensity ratio and the wall zeta potential were measured under the conditions with the ion seeds in the solution and the wall material being varied in a variety of ways. Their relationship is shown in FIG. 4.

TABLE 1

|      | pH (-) | c (mmol/L) |
|------|--------|------------|
| KCl  | 7.06   | 2.5        |
| NaCl | 7.13   | 2.5        |
| CaCl$_2$ | 7.14 | 1.0      |

TABLE 2

Borosilicate glass (BG)
Silica glass (SG)
Octadecyltrichlorosilane (OTS)

FIG. 4 shows that a good linearity over a wide range has been obtained which was impossible by the conventional nano-scale laser induced fluorescence imaging method disclosed in Non-Patent Document 9. Accordingly, in the graph of FIG. 4, the relationship between the fluorescence intensity ratio and the wall zeta potential can be determined by drawing a calibration curve using an approximation curve based on the least squares method, for example. This allows for quantitatively calculating the wall zeta potential distribution from the two-dimensional distribution of fluorescence intensity ratios. To measure the zeta potential, fluorescent particles of a diameter of 500 nm are mixed into a solution to measure the electroosmotic velocity in the vicinity of the wall surface, thereby calculating the wall zeta potential according to Equation (1) (Helmholtz-Smoluchowski equation) shown below.

[Equation 1]

$$\zeta = -\frac{\mu}{\varepsilon E} u_{eof} \quad (1)$$

In the equation above, $\zeta$ is the zeta potential [V], $\mu$ is the viscosity coefficient [Pa·s], $\varepsilon$ is the permittivity [C/V·m], E is the electric field strength [V/cm], and $u_{eof}$ is the electroosmotic velocity [m/s].

Example

Figure 5:
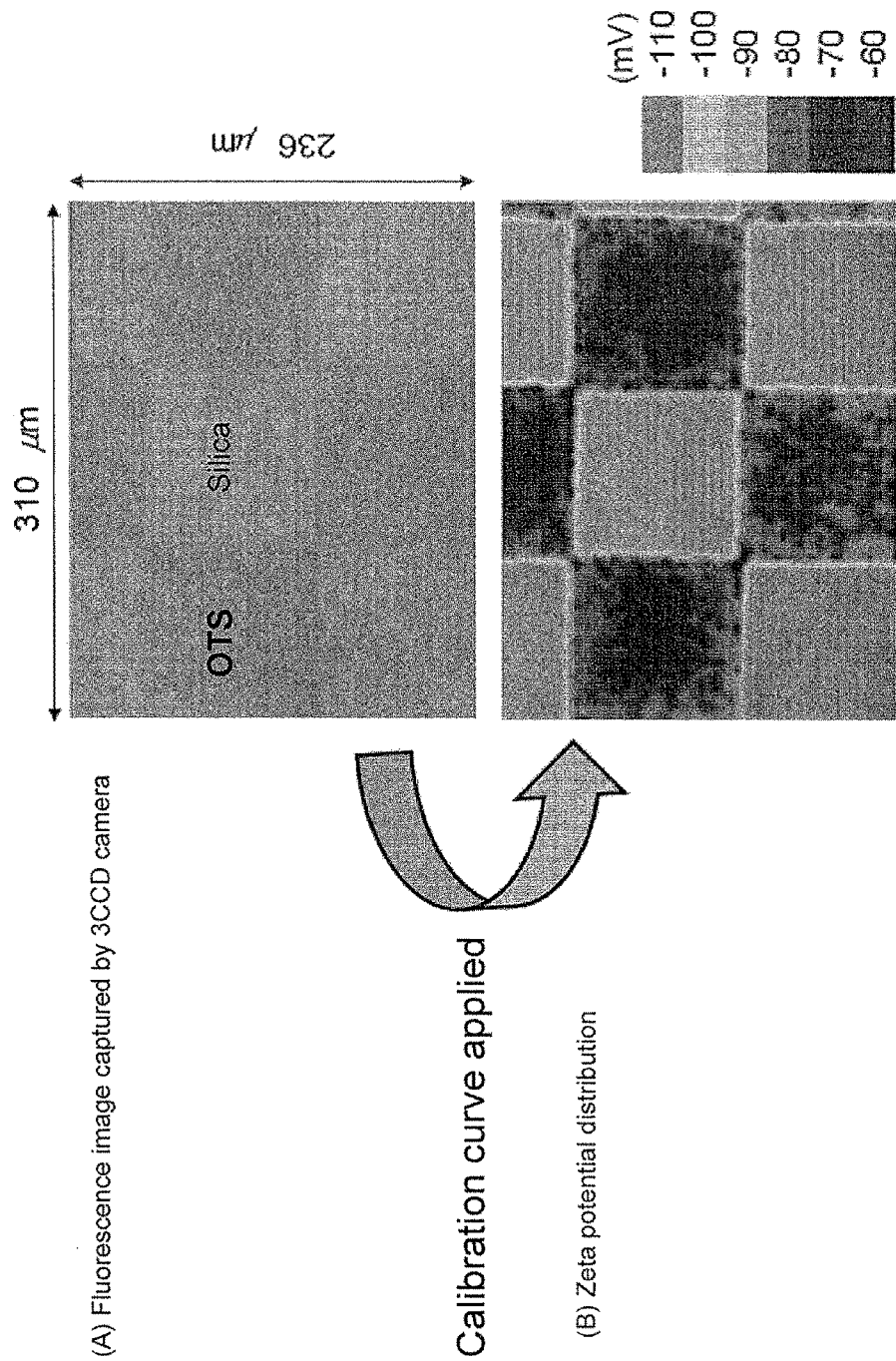
FIG. 5 is a view showing (A) an example of a zeta potential distribution on silica glass with a surface modification made to tiled OTS patterns of 100×100 μm, as taken by a 3CCD camera, and (B) an example of a quantitative evaluation of a zeta potential distribution using a calibration curve.

FIG. 5 shows the results of a real-time visualization and quantitative evaluation of the zeta potential that were obtained by applying the inventive measurement method to a piece of silica glass with a surface modification by octadecyltrichlorosilane (OTS) in the tile shape of 100×100 μm. As shown in FIG. 5(A), this technique allows for visualizing the two-dimensional distribution of zeta potentials formed by a surface modification applied to the wall surface of glass. The technique also made it possible to apply a calibration curve to quantitatively evaluate the two-dimensional distribution of zeta potentials as shown in FIG. 5(B).

Figure 6:
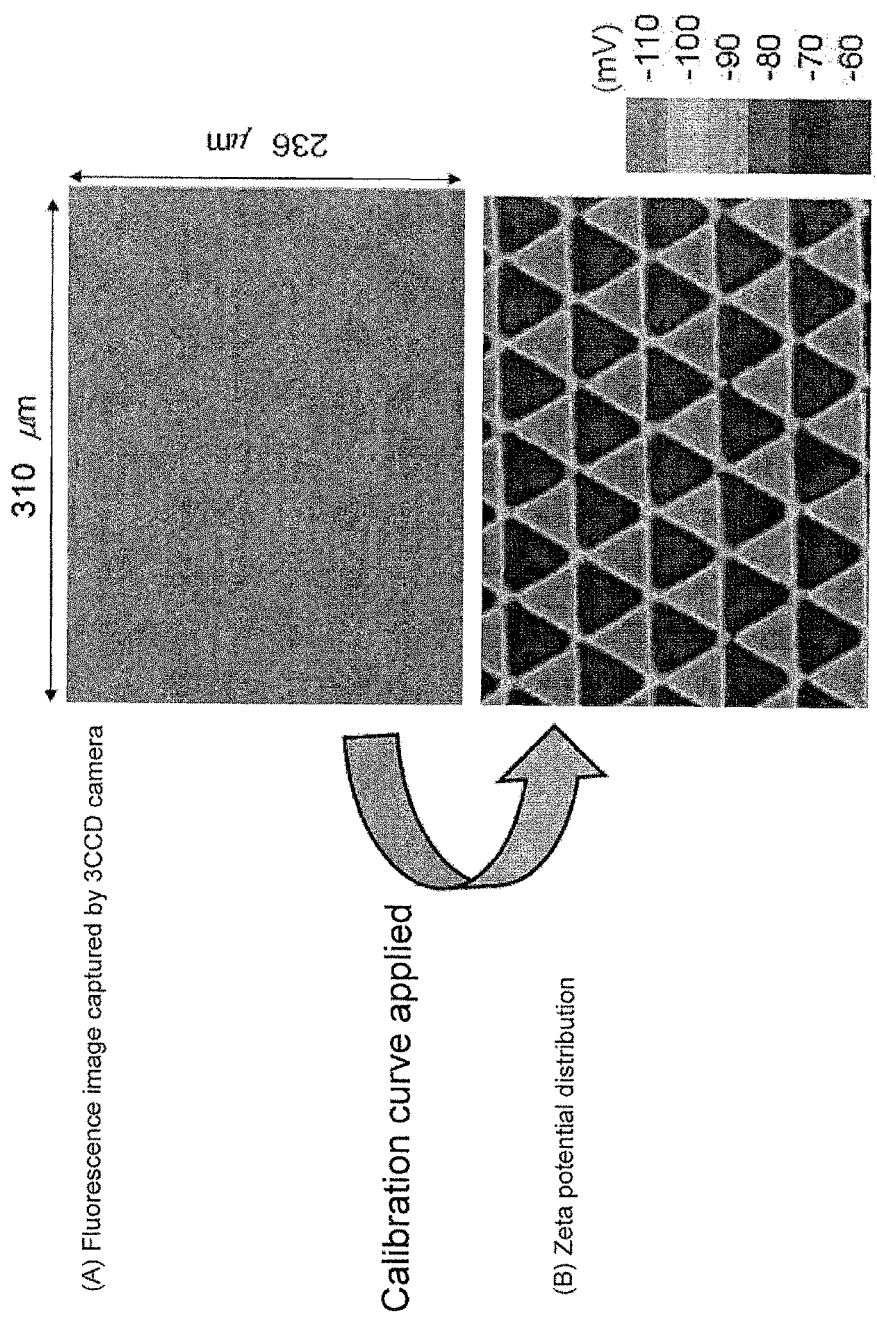
FIG. 6 is a view showing (A) an example of a zeta potential distribution on silica glass with a surface modification made to regular triangular OTS patterns having a side of 50 μm, as taken by a 3CCD camera, and (B) an example of a quantitative evaluation of a zeta potential distribution using a calibration curve.

FIGS. 6(A) and (B) show an example of a surface modification with OTS patterned in a regular triangle shape having a side of 50 μm.

The embodiment above has employed dichlorotris(1,10-phenanthroline) ruthenium(II) hydrate as a cation dye for emitting red light, while employing Alexa Fluor (registered trademark) 488 as an anion dye for emitting green light; however, the types of ions are not limited thereto. For example, it is possible to use Fluorescein (an excitation wavelength of 494 nm and a fluorescence wavelength of 518 nm) as an anion dye.

Furthermore, the combination of fluorescence colors is not limited to that of red and green; it is also possible to employ any combination of other two colors.

Furthermore, the two-dimensional imaging element is not limited to the 3CCD camera. It is also possible to employ MOS cameras or a plurality of cameras, for example, which can use filters to separate each color for imaging. The number of colors is not limited to three, either; any number of colors can be used as long as that number of colors corresponding to the number of the fluorescence colors (two colors in the embodiment) can be separated for imaging.

It is also possible to provide a plurality of lasers to cope with the excitation wavelength of each dye.

Furthermore, the present invention is not limited to the evaluation and visualization of the zeta potential distribution. The technique according to the present invention for making use of the ratio of two colors can be applied to the technique disclosed in Non-Patent Document 11 for obtaining the pH distribution and to the technique disclosed in Non-Patent Document 12 for obtaining the temperature distribution. These applications also enable the evaluation or visualization of the pH distribution and the temperature distribution. In these cases, for example, it is possible to employ LDS 698 (registered trademark) as a dye for obtaining a red fluorescence color and fluorescein as a dye for obtaining a green fluorescence color. Other than these dyes, it is also possible to use, for example, those listed in Table 2 on page 12 of Non-Patent Document 11: HPTS, Lucifer Yellow, rhodamine B, Sulforhodamine, Kiton Red, Phloxine B, and 1-4DHPN.

INDUSTRIAL APPLICABILITY

The present invention is applicable to quantitative evaluation of a wall zeta potential, pH, or temperature distribution in the fields of cell biology, electrochemistry, and micro/nanoscale thermo-fluid engineering, and to quantitative visualization of surface modifications.

The invention claimed is:

1. A method for quantitative evaluation of a wall zeta potential, pH, or temperature distribution, the method comprising:
   a step of mixing a first fluorescent dye and a second fluorescent dye into a solution, the first dye being positively ionized in the solution, and the second dye being negatively ionized in the solution and having a different fluorescence wavelength from the first dye;
   a step of flowing the solution onto a measured surface;
   a step of exciting the measured surface with an evanescent wave to thereby produce a fluorescence intensity distribution of two colors according to a concentration distribution of each fluorescent dye;
   a step of measuring a fluorescence intensity of the measured surface using a two-dimensional imaging element, the element being capable of providing a fluorescence intensity of each color separated from fluorescence intensities of the two colors;
   a step of calculating a ratio of the fluorescence intensities of the two colors; and a step of using a previously created equation expressing a relationship between the ratio of fluorescence intensities and a wall zeta potential, pH, or temperature to convert the distribution of the ratio of fluorescence intensities into a two-dimensional distribution of wall zeta potentials, pHs, or temperatures.

2. The method for quantitative evaluation of a wall zeta potential, pH, or temperature distribution according to claim 1, wherein the relationship between the fluorescence intensity ratio and the wall zeta potential, pH, or temperature is calibrated.

3. The method for quantitative evaluation of a wall zeta potential, pH, or temperature distribution according to claim 1, wherein the first dye is dichlorotris(1,10-phenanthroline) ruthenium(II) hydrate, which emits red light, and the second dye emits green light.

4. The method for quantitative evaluation of a wall zeta potential, pH, or temperature distribution according to claim 1, wherein, the two-dimensional imaging element is a single 3CCD camera.

5. An apparatus for quantitative evaluation of a distribution of wall zeta potentials, pHs, or temperatures, the apparatus comprising:
    means for flowing a solution mixed with a first fluorescent dye and a second fluorescent dye, the first dye being positively ionized in the solution, and the second dye being negatively ionized in the solution and having a different fluorescence wavelength from the first dye, onto a measured surface;
    means for exciting the measured surface with an evanescent wave to thereby produce a fluorescence intensity distribution of two colors according to a concentration distribution of each fluorescent dye;
    a two-dimensional imaging element being capable of providing a fluorescence intensity of each color separated from fluorescence intensities of two colors;
    means for calculating a ratio of the fluorescence intensities of the plurality of colors measured using the two-dimensional imaging element; and
    means for using a previously created equation expressing a relationship between the ratio of fluorescence intensities and a wall zeta potential, pH, or temperature to convert the distribution of the ratio of fluorescence intensities into a two-dimensional distribution of wall zeta potentials, pHs, or temperatures.

6. A method for quantitative visualization of a surface modification, the method comprising:
    a step of mixing a first fluorescent dye and a second fluorescent dye into a solution, the first dye being positively ionized in the solution, and the second dye being negatively ionized in the solution and having a different fluorescence wavelength from the first dye;
    a step of flowing the solution onto a measured surface, the measured surface having a localized distribution of zeta potentials, pHs, or temperatures due to a surface modification;
    a step of exciting the measured surface with an evanescent wave to thereby produce a fluorescence intensity distribution of two colors according to a concentration distribution of each fluorescent dye;
    a step of measuring a fluorescence intensity of the measured surface using a two-dimensional imaging element, the element being capable of providing a fluorescence intensity of each color separated from fluorescence intensities of the two colors;
    a step of calculating a ratio of the fluorescence intensities of the two colors; and
    a step of using a previously created equation expressing a relationship between the ratio of fluorescence intensities and a wall zeta potential, pH, or temperature to convert the distribution of the ratio of fluorescence intensities into a two-dimensional distribution of wall zeta potentials, pHs, or temperatures, thereby visualizing a surface modification pattern.

7. The method for quantitative visualization of a surface modification according to claim 6, wherein the surface modification is made by octadecyltrichlorosilane.

8. An apparatus for quantitative visualization of a surface modification, the apparatus comprising:
    means for flowing a solution mixed with a first fluorescent dye and a second fluorescent dye, the first dye being positively ionized in the solution, and the second dye being negatively ionized in the solution and having a different fluorescence wavelength from the first dye, onto a measured surface, the measured surface having a localized distribution of zeta potentials, pHs, or temperatures due to a surface modification;
    means for exciting the measured surface with an evanescent wave to thereby produce a fluorescence intensity distribution of two colors according to a concentration distribution of each fluorescent dye;
    a two-dimensional imaging element being capable of providing a fluorescence intensity of each color separated from fluorescence intensities of the two colors,
    means for calculating a ratio of the fluorescence intensities of multiple colors measured using the two-dimensional imaging element; and
    means for using a previously created equation expressing a relationship between the ratio of fluorescence intensities and a wall zeta potential, pH, or temperature to convert the distribution of the ratio of fluorescence intensities into a two-dimensional distribution of wall zeta potentials, pHs, or temperatures, thereby visualizing a surface modification pattern.

* * * * *